United States Patent [19]

Otten

[11] Patent Number: 5,493,215
[45] Date of Patent: Feb. 20, 1996

[54] APPARATUS FOR MEASURING THE PROPORTION OF PARAMAGNETIC SUBSTANCES IN CANCELLING A MIXTURE OF SUBSTANCES AND INCLUDING A COMPENSATING DEVICE FOR CANCELLING AN UNWANTED SIGNAL

[75] Inventor: Johann Otten, Bad Schwartau, Germany

[73] Assignee: Drägerwerk Aktiengesellschaft, Lübeck, Germany

[21] Appl. No.: 203,042

[22] Filed: Feb. 28, 1994

[30] Foreign Application Priority Data

Feb. 27, 1993 [DE] Germany .......................... 43 06 183.4

[51] Int. Cl.⁶ .......................... G01N 27/74; G01R 33/12
[52] U.S. Cl. .......................... 324/204; 324/225; 73/25.02
[58] Field of Search ...................... 324/204, 225, 324/228, 262; 73/25.02; 310/155, 168, 268, 261

[56] References Cited

U.S. PATENT DOCUMENTS 2,467,211   4/1949   Hornfeck ................................ 324/204
2,689,332   9/1954   Greene ................................... 73/25.02
4,763,509   8/1988   Albarda et al. ..................... 324/204 X
4,950,984   8/1990   Otten et al. .............................. 324/204

Primary Examiner—Sandra L. O'Shea
Assistant Examiner—Jay M. Patidar
Attorney, Agent, or Firm—Walter Ottesen

[57] ABSTRACT

An apparatus for determining the paramagnetic characteristics of substances such as oxygen includes a cuvette rotating in a magnetic field. The cuvette includes measuring chambers and reference chambers and an alternating voltage is induced in the measuring field coils by the rotation of the cuvette along the magnetic field. A base signal disturbing the measuring signal is also generated. This base signal is caused primarily by changes in the thickness of the material in the reference chambers and the measuring chambers and/or by material thickness changes of the cuvette. To eliminate this base signal, the cuvette includes a magnetic compensating device. This device is mounted at such a position that it generates a compensating magnetic field during its rotation through the magnetic field. This compensating field generates a compensating voltage which has the same amplitude as the base signal but has a signal waveform which is opposite in phase to the base signal.

6 Claims, 2 Drawing Sheets

APPARATUS FOR MEASURING THE PROPORTION OF PARAMAGNETIC SUBSTANCES IN CANCELLING A MIXTURE OF SUBSTANCES AND INCLUDING A COMPENSATING DEVICE FOR CANCELLING AN UNWANTED SIGNAL

FIELD OF THE INVENTION

The invention relates to an apparatus for measuring the proportion of paramagnetic substances such as oxygen in a mixture of substances. In the apparatus, a cuvette is rotated in a magnetic field which alternately penetrates a measuring chamber filled with the paramagnetic substance to be detected and a reference chamber filled with a reference material. During rotation, a magnetic alternating field is produced because of the different magnetic fluxes through the measuring chambers and the reference chambers, respectively. The magnetic alternating field generates an induction alternating voltage signal in one or in several measuring field coils. The induction alternating voltage signal is composed of a measuring signal caused by the measuring chambers and a reference signal produced by the reference chambers. The induction alternating voltage signal is applied as an index for the concentration of paramagnetic substance in the cuvette chambers and is conducted to an evaluation unit.

BACKGROUND OF THE INVENTION

A gas measuring apparatus off this kind for making a paramagnetic determination of oxygen is disclosed in U.S. Pat. No. 2,689,332. This apparatus includes a plurality of chambers which are each filled with the gas to be investigated having paramagnetic characteristics. A specific number of measuring chambers with a like number of reference chambers is guided along in pairs between the pole shoes of an even number of permanent magnets. Changes in the permeability of the cuvette material during rotation are compensated because of the series connection of the measuring field coils about the permanent magnets. This is so because the generated flux changes are opposite in phase. Possible changes of the permeability, which are still not compensated, can be compensated by applying small quantities of paramagnetic material to the cuvette disc. Suitable material for this purpose is red iron oxide.

A disadvantage in this known apparatus is the complex determination of suitable locations for the application of the additional paramagnetic material and the control as to whether the quantity of materials is adequate. Inconsistencies which remain must be compensated by downstream signal processing circuits.

A further apparatus of the type described above is disclosed in U.S. Pat. No. 4,950,984. The apparatus can be utilized for gas analysis as well as for monitoring waste water.

In the known apparatus, a disc-shaped cuvette rotates in a magnetic field which is generated by permanent magnets and which penetrates the cuvette. The measuring chambers of the cuvette comprise simple breakthroughs in the disc. The hollow spaces defined in this manner are flushed by the measuring gas to be investigated. The measuring chambers are separated from each other by a strip made of the material of the cuvette disc. This strip has a width which is more or less wide. This strip of material serves as a reference chamber filled with the material of the cuvette disc.

During the rotation of the cuvette, the measuring chambers for the gas to be measured or the cuvette disc material is passed by the magnetic field sources in dependence upon the number of measuring chambers. If a measuring gas such as oxygen is in the measuring chamber, then the paramagnetic characteristics of the measuring gas change the magnetic flux through the measuring chamber whereby an electric induction field is generated in a measuring field coil surrounding the magnetic field source.

It is desirable that disturbance signals are eliminated to the extent that even the smallest quantity of measuring gas can be detected without difficulty in order to obtain a measuring apparatus having the highest possible sensitivity. In addition to the suppression of disturbance signals, it is also necessary to have a stable zero value calibration at which the so-called zero signal is determined. This can be achieved in a simple manner in that, for example, nitrogen is used as a calibrating gas so that a paramagnetically generated induction signal is precluded. The calibration signal obtained in this manner however still contains a disturbing base signal. The cause of this is that the cuvette disc has different material thicknesses; that is, in the region of the measuring chamber, the measuring gas charge and possible thin chamber walls are to be considered and, in the area of the reference chamber region, the full material thickness of the cuvette disc or a reference chamber having a different gas content as reference gas is to be considered. In all cases, the thickness difference between the material of the reference chamber and of the measuring chamber is considerable so that the base signal is larger by a multiple than a minimum useful signal for the oxygen portion. The minimum useful signal is detectable because of the configuration of the apparatus.

As a rule, the cuvette disc is made of a diamagnetic material which can be magnetically neutralized by admixing paramagnetic or ferrimagnetic material. Even with this configuration, this method is complex and a cuvette disc produced in this manner cannot be changed subsequently in its magnetic characteristics with respect to the suppression of the base signal. Even if the neutralized diamagnetic disc itself would supply only a slight amount to the base signal, the fact would nonetheless remain that a disturbing base signal is generated because of the considerable thickness differences between the measuring gas and the reference material.

SUMMARY OF THE INVENTION

In view of the above, it is an object of the invention to provide an apparatus of the kind described above which is so improved that a cuvette is included therein having a material characteristic which induces no disturbing influence on the magnetically induced alternating voltage signal generated by the paramagnetic substance.

It is another object of the invention to provide compensating devices which can be placed specifically and reproducibly at suitable positions and can be adapted to the mechanical and geometric conditions.

The apparatus of the invention is for measuring the proportion of a paramagnetic substance such as oxygen in a mixture of substances and includes: a housing defining a longitudinal axis and having a first longitudinal end and a second longitudinal end opposite said first longitudinal end; a cuvette disposed between the longitudinal ends and having a measuring chamber filled with the paramagnetic substance and a reference chamber filled with a reference material;

magnetic field means for generating a magnetic field; drive means for rotating the cuvette in the magnetic field so as to cause the magnetic field to alternately penetrate the measuring and reference chambers to produce a magnetic alternating field because of different magnetic fluxes in respective ones of the chambers; measuring field coil means mounted in the housing adjacent the cuvette and being subjected to the magnetic alternating field whereby an inductive alternating voltage signal is induced in the measuring field coil means because of the material thickness differences between the measuring and reference chambers; the voltage signal being a composite signal defining an index for the concentration of the paramagnetic substance in the measuring chamber; the composite signal including a measuring signal component caused by the measuring chamber and a reference signal component caused by the reference chamber; the cuvette defining a rotational plane and having a magnetic compensating device mounted thereon in the rotational plane; the magnetic compensating device including an induction loop made of electrically conductive material and the induction loop having a terminating resistor; and, the induction loop being mounted at a predetermined location on the cuvette whereat the induction loop generates a compensation voltage in the measuring field coil means during the rotation of the cuvette with the compensation voltage having the same amplitude as the composite signal but having a waveform opposite in phase thereto.

The advantage of the invention can be seen in that the compensating device can be applied to the cuvette after determining the level and phase location of the base signal. A direct test of the effectiveness of the compensation is possible. Furthermore, necessary corrections to the compensating device can be easily effected. A basic advantage is that the base signal caused by induction is, in turn, eliminated by a compensating signal by means of a magnetic induction from the same magnetic field sources. In this way, both the disturbing base signal as well as the correcting compensating signal are based on the same physical laws of magnetic induction so that the compensation of the base signal is not burdened by additional system errors. In this way, disturbing drift effects (such as temperature drift), to which especially electronic circuits for compensating for disturbing signals are susceptible, are also eliminated. Furthermore, a complex subsequent signal processing is avoided because the disturbing signal (base signal) is immediately eliminated at the location of its origin.

As a rule, the cuvettes for an apparatus for determining paramagnetic characteristics of substances are made of a diamagnetic material in order to suppress an influence on the substance to be detected having paramagnetic characteristics. During the rotation of such a cuvette, thickness fluctuations in the region of the cuvette material itself as well as in the region of the different thicknesses for the measuring gas as well as for the reference gas are to be considered. Cuvette material which is not present or thin diamagnetic cuvette material operates as paramagnetic material on the signal.

The base signal generated in this manner is compensated by a material applied at a point on the cuvette at a radial spacing to the axis of rotation. The material is made of a substance which is paramagnetic, ferromagnetic or ferrimagnetic. The material is applied to the surface of the cuvette at such a location viewed in the rotational direction of the cuvette that the material generates a compensating signal in the measuring field coils which is electrically shifted in phase by 180°.

A circular disc made of diamagnetic material is selected as a simple configuration for the cuvette. Rotationally symmetrical cutouts are provided in the circular disc through which the paramagnetic substance to be detected flows.

The material generating the compensating magnetic field is then applied between two mutually adjacent cutouts at the bisecting angle. The cuvette can be seen as a chopper disc. The cutouts of the cuvette have significance for the induction signal in the measuring field coils in that the absent diamagnetic material is viewed in the same manner with respect to measuring as the paramagnetic material which is present. In this way, for each passthrough of the cutouts through the magnetic field, not only the paramagnetic characteristics of the gas to be investigated are detected but also a base signal from the fact that the diamagnetic material of the chopper disc is absent in the cutout and this is evaluated as a contribution to the measuring signal of a paramagnetic substance to be detected.

The base signal arising as described above is compensated by placing the paramagnetic material symmetrically between two mutually adjacent cutouts. If the chopper disc is provided with two opposite lying cutouts, then the compensating material is placed at a geometric angle of 90° between the two cutouts. On the other hand, if four cutouts arranged symmetrically with respect to each other are provided, then the compensating material is applied at a 45° angle to the adjacent cutout. The case can also be considered wherein only a single cutout is provided in the chopper disc. In this case, the compensating material is applied to the side lying opposite the cutout at an angle of 180° to the cutout.

A further possibility for applying a compensating device comprises that the compensating device is an induction loop made of electrically-conductive material. The induction loop includes a terminating resistor and is applied to the cuvette arrangement in the plane of rotation. A voltage is induced in the induction loop for a suitable magnitude of the terminating resistor when the magnetic field is passed through. This voltage generates a current in the loop in dependence upon the magnitude of the resistance which, in turn, permits a magnetic field to occur which acts in opposition to the induced magnetic field. By measuring the induced magnetic field voltages, a determination can be made in a simple manner on which circular angle of the rotating cuvette arrangement the induction loop is to be placed in order to generate the compensating field.

The induction loop is made of electrically conductive material and has a terminating resistor so that a current is produced in the loop in dependence upon the magnitude of the terminating resistor as the cuvette rotates in the magnetic field thereby, in turn, generating a compensating field.

The induction loop is mounted at a predetermined location on the cuvette whereat the induction loop generates, via the compensating field, a compensation voltage in the measuring field coil during the rotation of the cuvette with the compensation voltage having the same amplitude as the unwanted base signal but having a waveform opposite in phase thereto.

A suitable embodiment of the induction loop comprises that the loop extends in the radial direction on the cuvette so that the loop has a long axis of symmetry lying on a radius of the cuvette.

The cuvette can comprise a circular disc made of diamagnetic material in which cutouts are provided symmetrically to the axis of rotation. The paramagnetic substance to be detected can flow through the cutouts. If the cuvette is as described above, then it is advantageous to mount the loop after the cutout viewed in the direction of rotation at such an angular position that the loop corresponds to the fourth part of the angle between mutually adjacent cutouts. If for example two cutouts are provided which lie diametrically opposite each other, then the induction loop is to be applied at an angle of 45° viewed in the rotational direction after the adjacent cutout. The geometric angle of 45° corresponds to an electrical phase angle of 90° (lagging) since two induction cycles per rotation take place because of the two mutually adjacent cutouts of the chopper disc (180° geometric corresponds to 360° electric).

The location for placing the induction loop can be derived from the following. The cutout in the chopper disc generates a time-dependent change of the magnetic flux in the measuring field coils. From this, a 90° phase shift results for the induced voltage in the measuring field coils with respect to the magnetic flux. The induction loop on the chopper disc likewise detects a time-dependent change of the magnetic flux whereby the voltage generated therein is likewise shifted by 90° with respect to the magnetic flux so that these two 90° phase shifts are cancelled. The induction current flowing in the induction loop because of the generated voltage generates, in turn, a magnetic field which generates a voltage in the measuring field coils because of the time-dependent change of the magnetic flux of the induction loop. This voltage is shifted in phase by a further 90°. Overall, together with the 90° from the 45° shift of the induction loop, a phase shift of 180° is obtained.

The arrangement of an induction loop with a terminating resistor makes a simple correction of the compensating effect possible by changing the resistance value. Furthermore, this resistance value is stable with respect to temperature so that a temperature drift of the compensating resistor can be precluded. An induction loop of this kind with the resistor is inexpensive in thick film technology and can be produced in a manner similar to printed circuits. The material of the cuvette can be selected from a highly pure silicon so that a compensation of the induction coil is possible by laser treatment of the thick film.

A further advantageous possibility for applying a compensating device is seen in that an electrically-conductive film is applied to the surface of the cuvette in its plane of rotation. Eddy currents are induced in this film which permit the film to operate outwardly as an induction loop. The compensating effect of the film can be adjusted by its form, its size or also by its film thickness and can be corrected after being applied to the cuvette surface by means of grinding or laser treatment. Such a film can be applied simply as metal film by adhesive or as thick layer film by printing onto the surface of the cuvette. The determination of the phase position of the compensating signal is provided in the same manner as with the induction loop.

The selection of an induction loop or an electrically-conductive film can be made still more effective by adjusting its shape. The form, for example of the metal film, is so selected that a trace of the magnetic flux in the metal film occurs with this trace being reasonably sinusoidal in shape. An induced voltage results from this having an approximately sinusoidal shape. The voltage is characterized by a paucity of harmonics and a simplification of the signal processing. The suitable configuration of the induction loop and metal film can be easily determined on the compensating device, which is applied to the surface, by changing the shape.

All signals, which are based on a change of magnetic flux, exhibit a high content of harmonics in the induced voltage and this makes signal processing difficult. In addition, the time-dependent change of the magnetic flux leads to a proportionality between the frequency (that is, the rpm of the cuvette) and the measuring voltage. This makes a precise rpm control necessary. Both difficulties are overcome in that the induced alternating voltage signal is supplied to an integrator as a preamplifier. The harmonics are reduced in this way. The dependency upon frequency is also compensated for because the transfer function of an integrator is inversely proportional to the frequency. Finally, an integrator has a phase of 90° at each frequency. This is an advantage with respect to band-limiting preamplifiers which exhibit a dependency of their phase on the frequency or on the rpm. A precise rpm control is thereby unnecessary.

The cutouts of the cuvette are advantageously arranged concentric to the rotational axis and are configured as circular annular segments. The cutouts can likewise advantageously have a contour running kidney-shaped concentrically to the axis of rotation.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
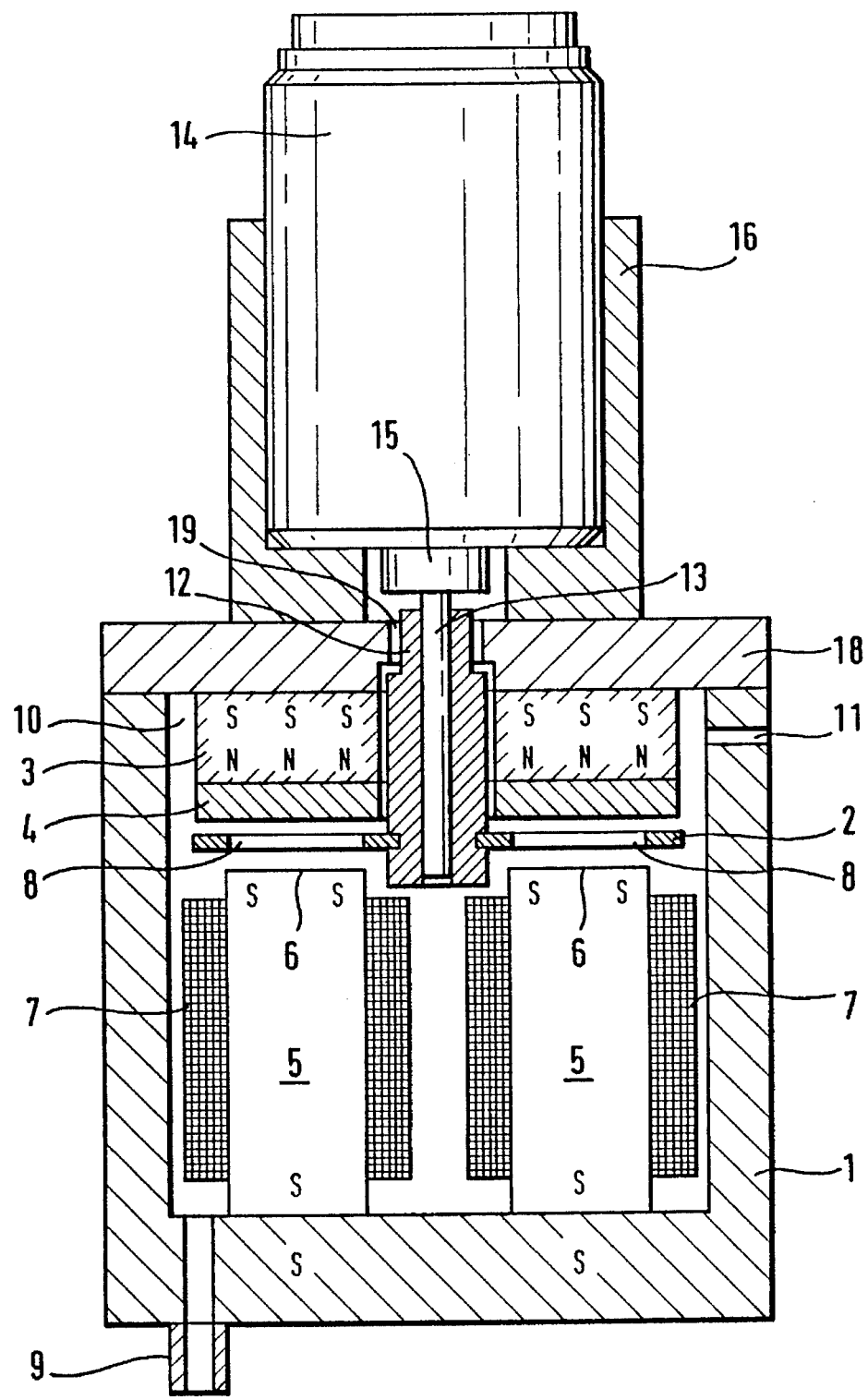
FIG. 1 is a side elevation view, in section, of a paramagnetic measuring apparatus according to the invention.

FIG. 1 shows an apparatus housing 1 containing a cuvette 2 in the form of a disc rotatively journalled on a shaft 13. The disc is made of magnetic material which is as inert as possible. The cuvette 2 rotates in the housing 1 between a permanent magnetic plate 3 and four iron cores 5 of which only two are shown. The permanent magnetic plate 3 is covered by an equipotential plate 4. Each of the cores 5 is surrounded by a measuring field coil 7. A signal line extends from each measuring field coil to an evaluation unit (not shown).

The cuvette 2 has rotationally-symmetrical cutouts 8 which expose the end faces 6 of the cores 5 with respect to the magnetic plate 3 in the position shown. The interior space of the cutouts 8 is filled with a substance (for example oxygen) to be measured and having paramagnetic characteristics. The substance is introduced into the interior space of the housing 1 via the gas feed 9 which is also suitable for supplying liquid in the case of an aqueous sample. The substance then fills the interior space of the housing and penetrates into the vicinity of the cutouts 8 and the cuvette 2 with this vicinity defining the measuring chamber 10. From there, the substance escapes via an outlet 11 to the ambient.

The cuvette 2 is secured on a shaft lug 12 which, in turn, is attached to the shaft 13 of a drive motor 14 and the shaft is guided by a shaft bearing 15. The motor 14 and the motor mount 16 surrounding the motor are connected to the housing wall 18. The housing wall 18 supports the magnetic plate 3 on the one hand and has a breakthrough 19 for the shaft 13 and the shaft lug 12 on the other hand. The magnetizing polarity of the magnetic plate 3 is shown by N (north) and S (south).

Figure 2:
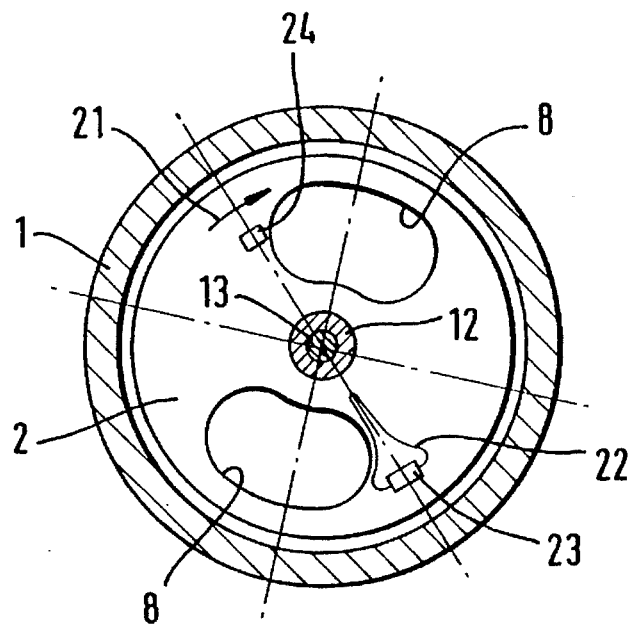
FIG. 2 is a plan view of the cuvette equipped with an induction loop and a metal platelet; and, FIG. 3 is a plan view of a cuvette arrangement having a compensating device in the form of a platelet made of a paramagnetic substance.

FIG. 2 shows a plan view of the cuvette 2 with the section view being taken through the housing 1 at the elevation of the surface of the cuvette disc 2 facing toward the iron cores 5. That surface of the cuvette 2 is shown which is facing toward the end faces 6 of the cores 5 (not shown). The end faces 6 are positioned above the plane of the drawing at the elevation of the symmetry axis (shown by dot-dashed lines) of the cuvette disc 2.

The cuvette 2 is configured to be in the form of a thin disc which rotates about the shaft lug 12 and has two approximately kidney-shaped cutouts 8. These cutouts 8 are filled with a gas or with a liquid having paramagnetic characteristics. The gas can, for example, be oxygen. The rotational direction of the cuvette disc 2 is indicated by the directional arrow 21.

A compensating device in the form of an induction loop 22 closed upon itself is shown at an angle of 45° to the connecting line (symmetry axis) between the two cutouts 8. The induction loop 22 is completed with a compensating resistor 23. A metal platelet 24 lies diametrically opposite the induction loop 22 on the same radial connecting line. The induction loop 22 and the compensating resistor 23 as well as the metal platelet 24 serve as compensating device for the base signal which is produced in the magnetic field coils 7 by the alternating overflights of the cutouts 8 and of the cuvette material disposed between the cutouts 8. The overflight occurs in the direction of directional arrow 21 along the cores 5.

Figure 3:
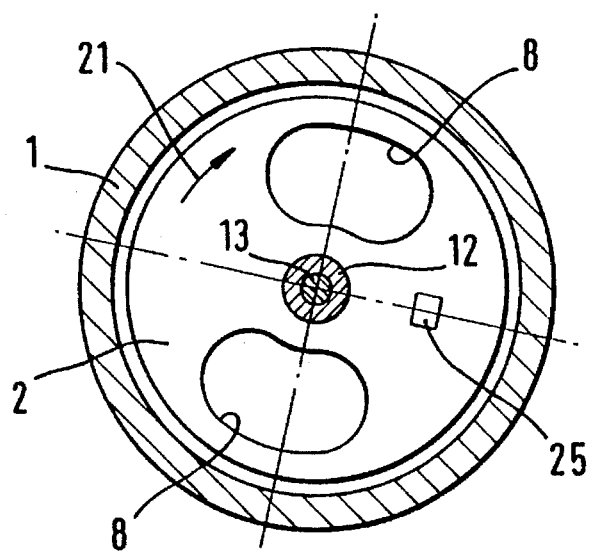

FIG. 3 shows the same cuvette 2 as shown in FIG. 2. However, here the compensating device is in the form of a rectangular platelet 25 made of paramagnetic material. The platelet is disposed at an angle of 90° to the connecting line and is between the two cutouts 8.

It is understood that the foregoing description is that of the preferred embodiments of the invention and that various changes and modifications may be made thereto without departing from the spirit and scope of the invention as defined in the appended claims.

What is claimed is:

1. An apparatus for measuring the proportion of a paramagnetic substance such as oxygen in a mixture of substances, the apparatus comprising:

a housing defining a longitudinal axis and having a first longitudinal end and a second longitudinal end opposite said first longitudinal end;

a cuvette disposed between said longitudinal ends and having a measuring chamber filled with said paramagnetic substance and a reference region containing a reference material;

magnetic field means for generating a magnetic field;

drive means for rotating said cuvette in said magnetic field so as to cause said magnetic field to alternately penetrate said measuring chamber and said reference region to produce a magnetic alternating field because of different magnetic fluxes in respective ones of said chamber and said reference region;

measuring field coil means mounted in said housing adjacent said cuvette and being subjected to said magnetic alternating field wherein an inductive alternating voltage signal is induced in said measuring field coil means;

said voltage signal being a composite signal defining an index for the concentration of said paramagnetic substance in said measuring chamber;

said composite signal including a measuring signal component caused by said measuring chamber and a reference signal component caused by said reference region;

said measuring chamber and said reference region having respective different material thickness wherein an unwanted base signal is generated in said measuring field coil means;

said cuvette defining a rotational plane and having a magnetic compensating device mounted thereon in said rotational plane;

said magnetic compensating device including an induction loop made of electrically conductive material and said induction loop having a terminating resistor so that a current is produced in said induction loop in dependence upon the magnetic of said field thereby, in turn, generating a compensating field; and, said induction loop being mounted at a predetermined location on said cuvette whereat said induction loop generates, via said compensating field, a compensation voltage in said measuring field coil means during the rotation of said cuvette with said compensation voltage having the same amplitude as said unwanted base signal but having a waveform opposite in phase thereto.

2. The apparatus of claim 1, said cuvette having a surface parallel to said rotational plane; and, said induction loop being mounted on said surface of said cuvette so as to extend radially outwardly.

3. The apparatus of claim 2, said drive means defining an axis of rotation about which said cuvette is rotated; said cuvette being a circular disc made of diamagnetic material and said measuring chamber being a first cutout formed in said circular disc for receiving a throughflow of said paramagnetic substance therein; said circular disc having a second cutout formed therein for likewise receiving a throughflow of said paramagnetic substance; said first and second cutouts being rotationally symmetrical with respect to said axis of rotation; said cutouts conjointly defining an angle therebetween; and, said loop being placed at such an angular position after one of said cutouts so that said angular position corresponds to a fourth part of said angle between said cutouts.

4. The apparatus of claim 3, said drive means defining an axis of rotation; said cutouts lying on an imaginary circle concentric to said axis of rotation; and, said cutouts being configured as annular slot segments extending along respective segments of said imaginary circle.

5. The apparatus of claim 3, said cutouts being configured so as to have a kidney-shaped contour concentric to said axis of rotation.

6. The apparatus of claim 1, said drive means defining an axis of rotation about which said cuvette is rotated; said cuvette having a surface parallel to said rotational plane; said induction loop being mounted on said surface along a radius on one side of said axis of rotation; and, said apparatus further comprising a metal platelet mounted on said surface diametrically opposite said induction loop.

* * * * *

UNITED STATES PATENT AND TRADEMARK OFFICE
CERTIFICATE OF CORRECTION

PATENT NO. : 5,493,215

DATED : February 20, 1996

INVENTOR(S) : Johann Otten

It is certified that error appears in the above-identified patent and that said Letters Patent is hereby corrected as shown below:

In the title on the title page and in column 1: delete "CANCELLING" (first occurrence).

In column 1, line 32: delete "off" and substitute -- of -- therefor.

In column 8, line 19: delete "magnetic" and substitute -- magnitude -- therefor.

In column 8, line 19: between "said" and "field", insert -- terminating resistor as said cuvette rotates in said magnetic --.

Signed and Sealed this

Fourth Day of June, 1996

*Attest:*

BRUCE LEHMAN

*Attesting Officer*     *Commissioner of Patents and Trademarks*